US00PP23228P2

(12) United States Plant Patent
Miedema-Jorna

(10) Patent No.: US PP23,228 P2
(45) Date of Patent: Nov. 27, 2012

(54) ***CALIBRACHOA* PLANT NAMED 'FICALLINPI'**

(50) Latin Name: ***Calibrachoa* sp.**
Varietal Denomination: Ficallinpi

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 13/134,178

(22) Filed: May 31, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — Annette Para
(74) *Attorney, Agent, or Firm* — C. A. Whealy

(57) ABSTRACT

A new and distinct cultivar of *Calibrachoa* plant named 'Ficallinpi', characterized by its upright, outwardly spreading and uniformly mounding plant habit; moderately vigorous growth habit; freely branching habit; freely flowering habit; light red purple-colored flowers; and good garden performance.

1 Drawing Sheet

Botanical designation: *Calibrachoa* sp.
Cultivar denomination: 'FICALLINPI'.

BACKGROUND OF THE INVENTION

The present invention relates to a new and distinct *Calibrachoa* plant, botanically known as *Calibrachoa* sp. and hereinafter referred to by the name 'Ficallinpi'.

The new *Calibrachoa* plant is a product of a planned breeding program conducted by the Inventor in De Lier, The Netherlands. The objective of the breeding program is to create new freely-branching *Calibrachoa* plants with compact and uniformly mounded plant habit, freely flowering habit and attractive leaf and flower coloration.

The new *Calibrachoa* plant originated from a cross-pollination made by the Inventor in 2005 in De Lier, The Netherlands of two unnamed proprietary selections of *Calibrachoa* sp., not patented. The new *Calibrachoa* plant was discovered and selected by the Inventor as a single flowering plant from within the progeny of the stated cross-pollination in a controlled greenhouse environment in De Lier, The Netherlands.

Asexual reproduction of the new *Calibrachoa* plant by vegetative cuttings in a controlled greenhouse environment in De Lier, The Netherlands since 2007 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environment conditions such as temperature and light intensity without, however, any variance in genotype.

The following traits have been repeatedly observed and are determined to be the unique characteristics of 'Ficallinpi'. These characteristics in combination distinguish 'Ficallinpi' as a new and distinct *Calibrachoa* plant:

1. Upright, outwardly spreading and uniformly mounding plant habit.
2. Moderately vigorous growth habit.

3. Freely branching habit.
4. Freely flowering habit.
5. Light red purple-colored flowers.
6. Good garden performance.

Plants of the new *Calibrachoa* can be compared to plants of the parent selections. Plants of the new *Calibrachoa* differ primarily from plants of the parent selections in plant habit and flower size as plants of the new *Calibrachoa* are more uniform and have larger flowers than plants of the parent selections.

Plants of the new *Calibrachoa* can be compared to plants of the *Calibrachoa* sp. 'Filindura Pink', disclosed in U.S. Plant Pat. No. 19,626. In side-by-side comparisons conducted in De Lier, The Netherlands, plants of the new *Calibrachoa* differed from plants of 'Filindura Pink' in the following characteristics:

1. Plants of the new *Calibrachoa* were more uniformly mounding than and not as trailing as plants of 'Filindura Pink'.
2. Plants of the new *Calibrachoa* and 'Filindura Pink' differed in flower color as plants of 'Filindura Pink' had darker red purple-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant. The photograph comprises a side perspective view of a typical flowering plant of 'Ficallinpi' grown in a container.

DETAILED BOTANICAL DESCRIPTION

The aforementioned photograph and following observations, measurements and values describe plants grown during the late spring and early summer in 10.5-cm containers in a glass-covered greenhouse in De Lier, The Netherlands and under commercial practices. During the production of the plants, day and night temperatures averaging 18° C. Plants were 13 weeks old when the photograph and description were taken. In the following description, color references are made to The Royal Horticultural Society Colour Chart, 2007 Edition, except where general terms of ordinary dictionary significance are used.

Botanical classification: *Calibrachoa* sp. 'Ficallinpi'.

Parentage:

*Female, or seed, parent*.—Unnamed proprietary selection of *Calibrachoa* sp., not patented.

*Male, or pollen, parent*.—Unnamed proprietary selection of *Calibrachoa* sp., not patented.

Propagation:

*Type*.—By vegetative cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white in color.

*Rooting habit*.—Freely branching; moderately dense.

Plant description:

*Plant and growth habit*.—Upright, outwardly spreading and uniformly mounding plant habit; moderately vigorous growth habit.

*Branching habit*.—Freely branching habit with about five primary lateral branches per plant each with multiple secondary lateral branches; pinching is typically not required.

*Plant height*.—About 7 cm.

*Plant diameter*.—About 27 cm.

Lateral branch description:

*Length*.—About 14 cm.

*Diameter*.—About 2 mm.

*Internode length*.—About 1 cm.

*Strength*.—Moderately strong.

*Aspect*.—Initially upright to outwardly spreading.

*Texture*.—Densely pubescent.

*Color*.—Close to 144A.

Foliage description:

*Arrangement*.—Alternate, simple; sessile.

*Length*.—About 2.3 cm.

*Width*.—About 8 mm.

*Shape*.—Ovate.

*Apex*.—Acute.

*Base*.—Attenuate.

*Margin*.—Entire.

*Texture, upper and lower surfaces*.—Densely pubescent.

*Venation pattern*.—Pinnate; arcuate.

*Color*.—Developing leaves, upper surface: Close to 143A. Developing leaves, lower surface: Close to 143C. Fully expanded leaves, upper surface: Close to N137A; venation, close to N137A. Fully expanded leaves, lower surface: Close to 138B; venation, close to 138B.

Flower description:

*Flower form, flower arrangement and flowering habit*.—Salverform flowers arranged singly arising from leaf axils; freely flowering habit with usually about 50 open flowers and flower buds developing per plant; flowers face upright to outwardly.

*Fragrance*.—None detected.

*Natural flowering season*.—Plants begin flowering about 6.5 weeks after planting; flowering continuous from the spring throughout the summer in The Netherlands.

*Flower longevity*.—Flowers last about five days on the plant; flowers persistent.

*Flower bud*.—Shape: Narrowly oblanceolate. Length: About 1.5 cm. Diameter: About 3 mm. Color: Close to N70A, 59A and 10A.

*Flower diameter*.—About 3.5 cm.

*Flower depth (height)*.—About 2.5 cm.

*Flower throat*.—About 1 cm.

*Flower tube length*.—About 1.5 cm.

*Flower tube diameter*.—About 2 mm.

*Corolla*.—Arrangement: Five petals fused at the base and opening into a flared trumpet. Petal lobe length: About 1.5 cm. Petal lobe width: About 1.5 cm. Petal shape: Spatulate. Petal apex: Retuse. Petal margin: Entire. Petal lobe texture, upper and lower surfaces: Smooth, glabrous. Petal tube texture: Densely pubescent. Color: Petal, when opening, upper surface: Close to N74D. Petal, when opening, lower surface: Close to N74C. Petal, fully opened, upper surface: Close to N74D; venation and star pattern, close to N79A; color does not fade with development. Petal, fully opened, lower surface: Close to N74C. Throat: Close to 13A; venation, close to 59C. Tube: Close to 10B; venation, close to 59C.

*Calyx*.—Arrangement: One star-shaped calyx tube with five fused sepals. Sepal length: About 1.3 cm. Sepal width: About 2 mm. Sepal shape: Narrowly oblong. Sepal apex: Acute. Sepal base: Cuneate. Sepal margin: Entire. Sepal texture, upper and lower surfaces: Densely pubescent. Sepal color, upper surface: Close to 138A. Sepal color, lower surface: Close to 138B.

*Peduncles*.—Length: About 1.8 cm. Diameter: About 1.5 mm. Angle: About 40° from stem axis. Strength: Moderately strong. Texture: Densely pubescent. Color: Close to 144B.

*Reproductive organs*.—Stamens: Quantity: Five per flower. Filament length: About 1 cm. Filament color: Close to 4B. Anther shape: Broadly reniform. Anther length: About 1 mm. Anther color: Close to 8B. Pollen amount: Moderate. Pollen color: Close to 10A. Pistils: Quantity: One per flower. Pistil length: About 1.1 cm. Style length: About 8 mm. Style color: Close to 145A. Stigma shape: Three-lobed, flattened. Stigma color: Close to 144A. Ovary color: Close to 145B. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 35° C.

Pathogen/pest resistance: Plants of the new *Calibrachoa* have not been observed to be resistant to pathogens and pests common to *Calibrachoa* plants.

It is claimed:

1. A new and distinct *Calibrachoa* plant named 'Ficallinpi' as illustrated and described.

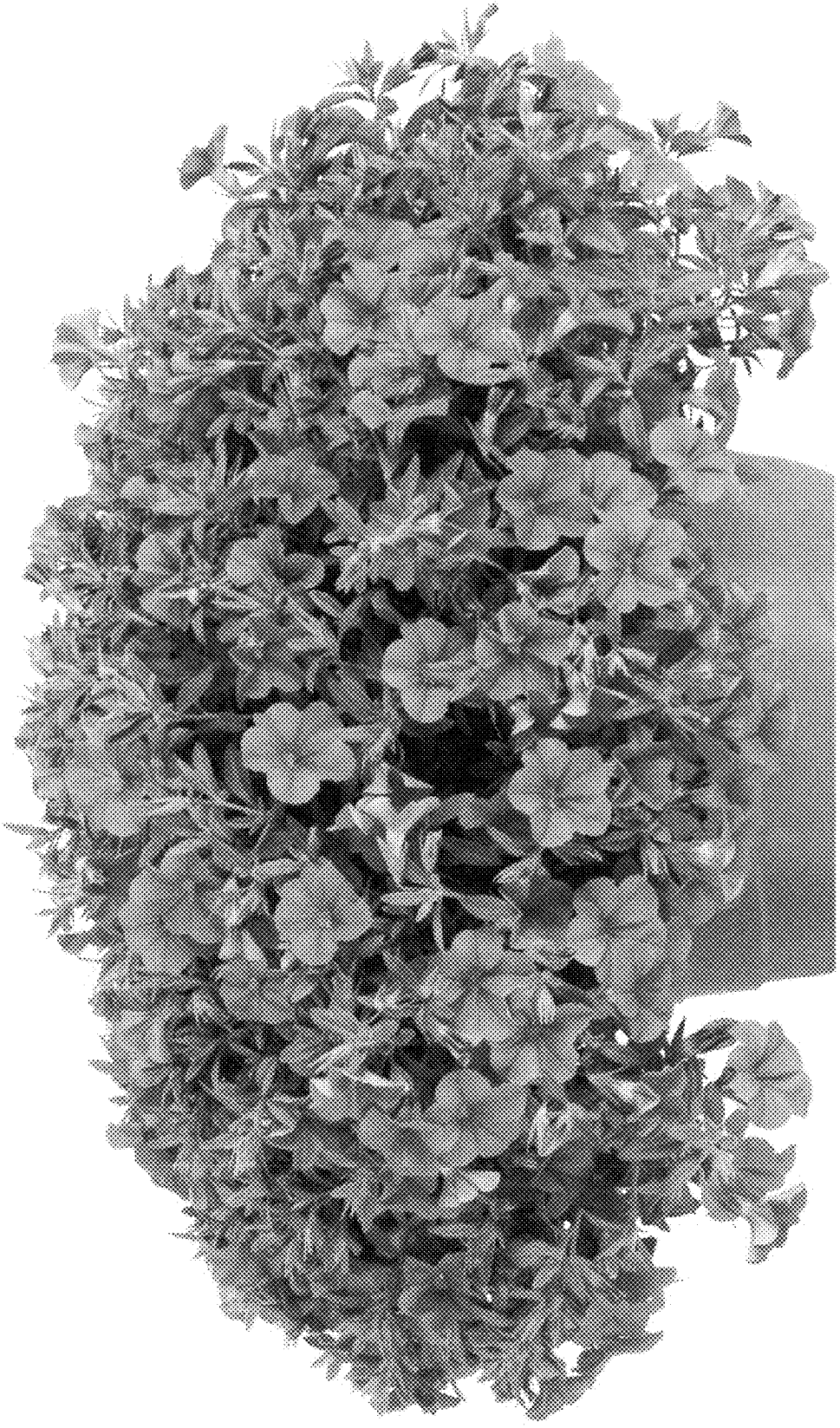

* * * * *